(12) United States Patent
Gebreselassie et al.

(10) Patent No.: US 9,737,479 B2
(45) Date of Patent: Aug. 22, 2017

(54) ORAL DELIVERY PRODUCTS INCLUDING THREE-DIMENSIONAL OBJECTS

(71) Applicant: THE ADDITIVE ADVANTAGE, LLC, North Reading, MA (US)

(72) Inventors: Petros Gebreselassie, WhiteHouse Station, NJ (US); Atsushi Ueminami, Nara (JP); Anilkumar Ganapati Gaonkar, Buffalo Grove, IL (US)

(73) Assignee: The Additive Advantage, LLC, North Reading, MA (US)

( * ) Notice: Subject to any disclaimer, the term of this patent is extended or adjusted under 35 U.S.C. 154(b) by 0 days.

(21) Appl. No.: 14/376,754

(22) PCT Filed: Feb. 6, 2013

(86) PCT No.: PCT/US2013/024882
§ 371 (c)(1),
(2) Date: Aug. 5, 2014

(87) PCT Pub. No.: WO2013/119627
PCT Pub. Date: Aug. 15, 2013

(65) Prior Publication Data
US 2015/0030646 A1    Jan. 29, 2015

Related U.S. Application Data (60) Provisional application No. 61/595,464, filed on Feb. 6, 2012, provisional application No. 61/595,479, filed on Feb. 6, 2012.

(51) Int. Cl.
*A61K 9/68* (2006.01)
*A61K 8/02* (2006.01)
(Continued)

(52) U.S. Cl.
CPC .......... *A61K 9/0058* (2013.01); *A23G 4/025* (2013.01); *A23G 4/043* (2013.01); *A23G 4/20* (2013.01); *A23G 4/205* (2013.01); *A61K 8/02* (2013.01)

(58) Field of Classification Search
CPC .......... A23G 4/025; A23G 4/043; A23G 4/20; A23G 4/205; A61K 8/02; A61K 9/0058
See application file for complete search history.

(56) References Cited

U.S. PATENT DOCUMENTS 6,599,542 B1    7/2003    Abdel-Malik et al.
7,597,752 B2   10/2009    Shastry et al.
(Continued)

FOREIGN PATENT DOCUMENTS

JP    51-115960    10/1976
JP    61-28349 A    2/1986
(Continued)

OTHER PUBLICATIONS

International Preliminary Report on Patentablity for International Application No. PCT/US2013/024882, issued Aug. 12, 2014.
(Continued)

*Primary Examiner* — Aradhana Sasan
(74) *Attorney, Agent, or Firm* — Lisa M. Warren, Esq.; Stanley F. Chalvire, Esq.; Morse, Barnes-Brown & Pendleton, P.C.

(57) ABSTRACT

An edible product and method for making an edible product including a core composition having at least one outer surface and at least one edible, three dimensional object secured to the at least one outer surface, where the object includes a binder material and a deliverable component selected from the group consisting of flavors, colors, sweeteners, actives, sensates, effervescent components, and combinations thereof. Also, a method for delivery of at least one
(Continued)

deliverable component including placing such products in the mouth of a user and releasing the deliverable component from the edible, three dimensional object.

27 Claims, 3 Drawing Sheets

(51) Int. Cl.
  *A23G 4/20* (2006.01)
  *A23G 4/02* (2006.01)
  *A23G 4/04* (2006.01)

(56) References Cited

U.S. PATENT DOCUMENTS

| | | |
|---|---|---|
| 2005/0031775 A1 * | 2/2005 | Signorino et al. ............ 426/661 |
| 2005/0220934 A1 | 10/2005 | Leadbeater et al. |
| 2007/0166430 A1 | 7/2007 | Stawski et al. |
| 2007/0231424 A1 | 10/2007 | Castro et al. |
| 2007/0231427 A1 | 10/2007 | Ream |
| 2007/0231435 A1 | 10/2007 | Ream et al. |
| 2009/0130179 A1 | 5/2009 | Lakkis et al. |
| 2010/0104688 A1 | 4/2010 | Andersen et al. |
| 2010/0136185 A1 | 6/2010 | Miladinov et al. |
| 2010/0166934 A1 | 7/2010 | Caiger et al. |
| 2010/0312652 A1 | 12/2010 | Boghani et al. |
| 2012/0021024 A1 | 1/2012 | Boghani et al. |

FOREIGN PATENT DOCUMENTS

| | | | |
|---|---|---|---|
| JP | 11-033084 A | 2/1992 | |
| JP | 8-505140 A | 6/1996 | |
| JP | 2002-121276 A | 4/2002 | |
| WO | WO 2007/124744 | 11/2007 | |
| WO | WO 2010/088519 A1 * | 8/2010 | ............... A61K 9/14 |

OTHER PUBLICATIONS

Supplementary European Search Report for European Application No. EP 13746716, dated Sep. 22, 2015.

* cited by examiner

ORAL DELIVERY PRODUCTS INCLUDING THREE-DIMENSIONAL OBJECTS

This application is the National Stage of International Application No. PCT/US2013/024882, filed Feb. 6, 2013, which claims the benefit of U.S. Provisional Application No. 61/595,464 filed Feb. 6, 2012 and U.S. Provisional Application No. 61/595,479 filed Feb. 6, 2012, the contents of all of which are incorporated herein by reference in their entirety.

FIELD OF THE INVENTION

The present invention is directed to oral delivery products including objects secured to a surface thereof. Specifically, the oral delivery product includes at least one three-dimensional, disintegrable object on the surface, the object including a deliverable component.

BACKGROUND OF THE INVENTION

Various oral delivery products, such as chewing gums, have long served as vehicles for delivery of components, such as flavors, sensates, actives, and the like. It is often desired to release such components from a product in a rapid manner, for example, within a few seconds of entry of the product into the mouth of the user. One problem, however, with the delivery of such components in a chewing gum is that the gum base used to form the chewing gum has a tendency to trap components and restrict their release. Some solutions have included encapsulating components or incorporating them into an outer coating of the product. Each of these solutions, however, rely upon mastication of the product and do not provide an easy and rapid release of the component from the product.

The present invention solves the deficiencies of prior products.

SUMMARY OF THE INVENTION

In one embodiment of the present invention, there is an edible product including: an oral delivery composition having at least one outer surface; and at least one edible, three dimensional object secured to the at least one outer surface.

In another embodiment, there is provided a chewing gum product including: a chewing gum composition having at least one outer surface; and at least one edible, three dimensional object secured to the at least one outer surface, the object including polyethylene glycol and at least one deliverable component selected from the group consisting of flavors, colors, sweeteners, actives, sensates, inorganic fillers, plasticizers, emulsifiers, surfactants, and combinations thereof.

In still other embodiments of the present invention, there may be a method of forming an edible product including the steps of: providing an oral delivery composition having at least one outer surface; providing a flowable composition including a deliverable component; depositing the flowable composition onto the at least one surface; and forming a solid three dimensional object from the flowable composition; where the flowable composition is compositionally different than the oral delivery composition.

The present invention may further provide a method of providing a rapid release of a flavor to a user including the steps of: providing an oral delivery product to a user, the oral delivery product having: at least one outer surface; and at least one edible, three dimensional object secured to the at least one outer surface, where the object includes a polymer and a flavor component; placing the oral delivery product in the mouth of the user; and allowing the object to disintegrate in the mouth of the user, thereby releasing the flavor.

Other embodiments of the present invention include a method of providing a rapid sensorial experience to a user including the steps of: providing an oral delivery product to a user, the oral delivery product having: an oral delivery composition having at least one outer surface; and at least one edible, three dimensional object secured to the at least one outer surface, where the object provides a rapid sensorial experience to a user; placing the oral delivery product in the mouth of the user; and allowing the object to disintegrate in the mouth of the user, thereby providing the sensorial experience to the user.

Other embodiments of the present invention include an oral delivery product including: an oral delivery composition having at least one surface; and an edible three dimensional object secured to the surface; where the edible three dimensional surface is capable of being disintegrated in the presence of a liquid within a desired period of time.

DETAILED DESCRIPTION OF THE INVENTION

The present invention provides an oral delivery product that delivers a component or a sensorial experience to a user in a rapid and efficient manner. In addition, the invention includes a product that provides an appealing and distinct look to the user. The oral delivery product may include any edible and acceptable composition, including, for example, chewing gums, confectioneries or "non-chewing gum candies", edible films, and the like. Products made via the present invention are further unique in that they include a three dimensional component (referred to herein as an "object") to deliver a deliverable component, which may be easily removed, even after processing the product, without destroying the other components during removal of the object. This allows re-use and salvage of the other components, such as chewing gum base and other components.

As used herein the transitional term "comprising," (also "comprises," etc.) which is synonymous with "including," "containing," or "characterized by," is inclusive or open-ended and does not exclude additional, unrecited elements or method steps, regardless of its use in the preamble or the body of a claim.

As used herein, the terms "bubble gum", "chewing gum" and "gum" are used interchangeably and are both meant to include any gum compositions.

The compositions of the present invention include an oral delivery composition, including, for example, chewing gums, non-chewing gum candies, and edible films. Suitable non-chewing gum candies include, for example, hard candy, soft candy, chewy candy, center-fill candy, multi-layer candy, cotton candy, pressed tablets, multi-layer pressed tablets, lozenges, edible films, nougat, caramel, frappe, granule, gummy candy, jelly candy, taffy, toffee, and the like.

In embodiments where the product includes a chewing gum composition, the chewing gum compositions generally include a chewing gum core, which includes a gum base that may include typical components generally found within a chewing gum. The gum base may include any component known in the chewing gum art. Such components may be water soluble, water-insoluble or a combination thereof. For example, the gum base may include elastomers, bulking agents, waxes, elastomer solvents, emulsifiers, plasticizers, fillers and mixtures thereof.

The elastomers (rubbers) employed in the gum base will vary greatly depending upon various factors such as the type of gum base desired, the consistency of gum composition desired and the other components used in the composition to make the final chewing gum product. The elastomer may be any water-insoluble polymer known in the art, and includes those gum polymers utilized for chewing gums and bubble gums. Illustrative examples of suitable polymers in gum bases include both natural and synthetic elastomers. For example, those polymers which are suitable in gum base compositions include, without limitation, natural substances (of vegetable origin) such as chicle, natural rubber, crown gum, nispero, rosidinha, jelutong, perillo, niger gutta, tunu, balata, guttapercha, lechi capsi, sorva, gutta kay, and the like, and mixtures thereof. Examples of synthetic elastomers include, without limitation, styrene-butadiene copolymers (SBR), polyisobutylene, isobutylene-isoprene copolymers, polyethylene, polyvinyl acetate and the like, and mixtures thereof.

The amount of elastomer employed in the gum base may vary depending upon various factors such as the type of gum base used, the consistency of the gum composition desired and the other components used in the composition to make the final chewing gum product. In general, the elastomer will be present in the gum base in an amount from about 10% to about 60% by weight, desirably from about 35% to about 40% by weight.

In some embodiments, the gum base may include wax. It softens the polymeric elastomer mixture and improves the elasticity of the gum base. When present, the waxes employed will have a melting point below about 60° C., and preferably between about 45° C. and about 55° C. The low melting wax may be a paraffin wax. The wax may be present in the gum base in an amount from about 6% to about 10%, and preferably from about 7% to about 9.5%, by weight of the gum base.

In addition to the low melting point waxes, waxes having a higher melting point may be used in the gum base in amounts up to about 5%, by weight of the gum base. Such high melting waxes include beeswax, vegetable wax, candelilla wax, carnuba wax, most petroleum waxes, and the like, and mixtures thereof.

In addition to the components set out above, the gum base may include a variety of other ingredients, such as components selected from elastomer solvents, emulsifiers, plasticizers, fillers, and mixtures thereof. The gum base may additionally include components that are found within the three dimensional object, as explained below.

The gum base may contain elastomer solvents to aid in softening the elastomer component. Such elastomer solvents may include those elastomer solvents known in the art, for example, terpinene resins such as polymers of alpha-pinene or beta-pinene, methyl, glycerol and pentaerythritol esters of rosins and modified rosins and gums such as hydrogenated, dimerized and polymerized rosins, and mixtures thereof. Examples of elastomer solvents suitable for use herein may include the pentaerythritol ester of partially hydrogenated wood and gum rosin, the pentaerythritol ester of wood and gum rosin, the glycerol ester of wood rosin, the glycerol ester of partially dimerized wood and gum rosin, the glycerol ester of polymerized wood and gum rosin, the glycerol ester of tall oil rosin, the glycerol ester of wood and gum rosin and the partially hydrogenated wood and gum rosin and the partially hydrogenated methyl ester of wood and rosin, and the like, and mixtures thereof. The elastomer solvent may be employed in the gum base in amounts from about 2% to about 15%, and preferably from about 7% to about 11%, by weight of the gum base.

The gum base may also include emulsifiers which aid in dispersing the immiscible components into a single stable system. The emulsifiers useful in this invention include glyceryl monostearate, lecithin, fatty acid monoglycerides, diglycerides, propylene glycol monostearate, and the like, and mixtures thereof. The emulsifier may be employed in amounts from about 2% to about 15%, and more specifically, from about 7% to about 11%, by weight of the gum base.

The gum base may also include plasticizers or softeners to provide a variety of desirable textures and consistency properties. Because of the low molecular weight of these ingredients, the plasticizers and softeners are able to penetrate the fundamental structure of the gum base making it plastic and less viscous. Useful plasticizers and softeners include lanolin, palmitic acid, oleic acid, stearic acid, sodium stearate, potassium stearate, glyceryl triacetate, glyceryl lecithin, glyceryl monostearate, propylene glycol monostearate, acetylated monoglyceride, glycerine, and the like, and mixtures thereof. Waxes, for example, natural and synthetic waxes, hydrogenated vegetable oils, petroleum waxes such as polyurethane waxes, polyethylene waxes, paraffin waxes, microcrystalline waxes, fatty waxes, sorbitan monostearate, tallow, propylene glycol, mixtures thereof, and the like, may also be incorporated into the gum base. The plasticizers and softeners are generally employed in the gum base in amounts up to about 20% by weight of the gum base, and more specifically in amounts from about 9% to about 17%, by weight of the gum base.

Plasticizers also include hydrogenated vegetable oils, such as soybean oil and cottonseed oils, which may be employed alone or in combination. These plasticizers provide the gum base with good texture and soft chew characteristics. These plasticizers and softeners are generally employed in amounts from about 5% to about 14%, and more specifically in amounts from about 5% to about 13.5%, by weight of the gum base.

Anhydrous glycerin may also be employed as a softening agent, such as the commercially available United States Pharmacopeia (USP) grade. Glycerin is a syrupy liquid with a sweet warm taste and has a sweetness of about 60% of that of cane sugar. Because glycerin is hygroscopic, the anhydrous glycerin may be maintained under anhydrous conditions throughout the preparation of the chewing gum composition.

In some embodiments, the gum base may also include effective amounts of bulking agents such as mineral adjuvants which may serve as fillers and textural agents. Useful mineral adjuvants include calcium carbonate, magnesium carbonate, alumina, aluminum hydroxide, aluminum silicate, talc, tricalcium phosphate, dicalcium phosphate, calcium sulfate and the like, and mixtures thereof. These fillers or adjuvants may be used in the gum base compositions in various amounts. Preferably the amount of filler, when used, will be present in an amount from about 15% to about 40%, and desirably from about 20% to about 30%, by weight of the gum base.

A variety of traditional ingredients may be optionally included in the gum base in effective amounts such as flavor agents and coloring agents, antioxidants, preservatives, and the like. For example, titanium dioxide and other dyes suitable for food, drug and cosmetic applications, known as F. D. & C. dyes, may be utilized. An anti-oxidant such as butylated hydroxytoluene (BHT), butylated hydroxyanisole (BHA), propyl gallate, vitamin E and mixtures thereof, may also be included. Other conventional chewing gum additives known to one having ordinary skill in the chewing gum art may also be used in the gum base.

The chewing gum compositions may include amounts of conventional additives selected from the group consisting of sweetening agents, plasticizers, softeners, emulsifiers, waxes, fillers, bulking agents (carriers, extenders, bulk sweeteners), mineral adjuvants, flavor agents and coloring agents, antioxidants, acidulants, thickeners, medicaments, oral care actives, such as remineralization agents, antimicrobials and tooth whitening agents, as described in U.S. Pat. No. 6,685,916, which is incorporated herein by reference in its entirety, and the like, and mixtures thereof. Some of these additives may serve more than one purpose. For example, in sugarless gum compositions, a sweetener, such as maltitol or other sugar alcohol, may also function as a bulking agent.

Bulk sweeteners include sugars, sugarless bulk sweeteners, or the like, or mixtures thereof. Bulk sweeteners generally are present in amounts of about 5% to about 99% by weight of the chewing gum composition.

Suitable sugar sweeteners generally include mono-saccharides, di-saccharides and polysaccharides such as but not limited to, sucrose (sugar), dextrose, maltose, dextrin, xylose, ribose, glucose, lactose, mannose, galactose, fructose (levulose), invert sugar, fructo oligo saccharide syrups, partially hydrolyzed starch, corn syrup solids, isomaltulose and mixtures thereof.

Suitable sugarless bulk sweeteners include sugar alcohols (or polyols) such as, but not limited to, sorbitol, xylitol, mannitol, galactitol, maltitol, hydrogenated isomaltulose (ISOMALT), lactitol, erythritol, hydrogenated starch hydrolysate, stevia and mixtures thereof.

Suitable hydrogenated starch hydrolysates include those disclosed in U.S. Pat. No. 4,279,931 and various hydrogenated glucose syrups and/or powders which contain sorbitol, maltitol, hydrogenated disaccharides, hydrogenated higher polysaccharides, or mixtures thereof. Hydrogenated starch hydrolysates are primarily prepared by the controlled catalytic hydrogenation of corn syrups. The resulting hydrogenated starch hydrolysates are mixtures of monomeric, dimeric, and polymeric saccharides. The ratios of these different saccharides give different hydrogenated starch hydrolysates different properties. Mixtures of hydrogenated starch hydrolysates, such as LYCASIN®, a commercially available product manufactured by Roquette Freres of France, and HYSTAR®, a commercially available product manufactured by SPI Polyols, Inc. of New Castle, Del., are also useful.

In some embodiments, high-intensity sweeteners may be used. Without being limited to particular sweeteners, representative categories and examples include:

(a) water-soluble sweetening agents such as dihydrochalcones, monellin, stevia, steviosides, rebaudioside A, glycyrrhizin, dihydroflavenol, and sugar alcohols such as sorbitol, mannitol, maltitol, xylitol, erythritol and L-aminodicarboxylic acid aminoalkenoic acid ester amides, such as those disclosed in U.S. Pat. No. 4,619,834, which disclosure is incorporated herein by reference, and mixtures thereof;

(b) water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1, 2,3-oxathiazine-4-one-2,2-dioxide (Acesulfame-K), the free acid form of saccharin, and mixtures thereof;

(c) dipeptide based sweeteners, such as L-aspartic acid derived sweeteners, such as L-aspartyl-L-phenylalanine methyl ester (Aspartame) and materials described in U.S. Pat. No. 3,492,131, L-alphaaspartyl-N-(2,2,4, 4-tetramethyl-3-thietanyl)-D-alaninamide hydrate (Alitame), N-[N-(3,3-dimethylbutyl)-L-aspartyl]-L-phenylalanine 1-methyl ester (Neotame), methyl esters of L-aspartyl-L-phenylglycerine and L-aspartyl-L-2,5-dihydrophenyl-glycine, L-aspartyl-2,5-dihydro-L-phenylalanine; L-aspartyl-L-(1-cyclohexen)-alanine, and mixtures thereof;

(d) water-soluble sweeteners derived from naturally occurring water-soluble sweeteners, such as chlorinated derivatives of ordinary sugar (sucrose), e.g., chlorodeoxysugar derivatives such as derivatives of chlorodeoxysucrose or chlorodeoxygalactosucrose, known, for example, under the product designation of Sucralose; examples of chlorodeoxysucrose and chlorodeoxygalactosucrose derivatives include but are not limited to: 1-chloro-1'-deoxysucrose; 4-chloro-4-deoxy-alpha-D-galactopyranosyl-alpha-D-fructofuranoside, or 4-chloro-4-deoxygalactosucrose; 4-chloro-4-deoxy-alpha-D-galactopyranosyl-1-chloro-1-deoxy-beta-D-fructo-furanoside, or 4,1'-dichloro-4,1'-dideoxygalactosucrose; 1',6'-dichloro1',6'-dideoxysucrose; 4-chloro-4-deoxy-alpha-D-galactopyranosyl-1,6-dichloro-1,6-dideoxy-beta-D-fructofuranoside, or 4,1',6'-trichloro-4,1',6'-trideoxygalactosucrose; 4,6-dichloro-4,6-dideoxy-alpha-D-galactopyranosyl-6-chloro-6-deoxy-beta-D-fructofuranoside, or 4,6,6'-trichloro-4,6,6'-trideoxygalactosucrose; 6,1',6'-trichloro-6,1',6'-trideoxysucrose; 4,6-dichloro-4,6-dideoxy-alpha-D-galacto-pyranosyl-1,6-dichloro-1,6-dideox y-beta-D-fructofuranoside, or 4,6,1',6'-tetrachloro4,6,1',6'-tetradeoxygalacto-sucrose; and 4,6,1',6'-tetradeoxysucrose, and mixtures thereof;

(e) protein based sweeteners such as thaumatococcus danielli (Thaumatin I and II) and talin;

(f) the sweetener monatin (2-hydroxy-2-(indol-3-ylmethyl)-4-aminoglutaric acid) and its derivatives; and (g) the sweetener Lo han guo (sometimes also referred to as "Lo han kuo").

The intense sweetening agents may be used in many distinct physical forms well-known in the art to provide an initial burst of sweetness and/or a prolonged sensation of sweetness. Without being limited thereto, such physical forms include free forms, such as spray dried, powdered, beaded forms, encapsulated forms, and mixtures thereof.

In general, an effective amount of intense sweetener may be utilized to provide the level of sweetness desired, and this amount may vary with the sweetener selected. The intense sweetener may be present in amounts from about 0.001% to about 3%, by weight of the chewing gum composition, depending upon the sweetener or combination of sweeteners used. The exact range of amounts for each type of sweetener may be selected by those skilled in the art.

Flavors (flavorings or flavor agents), which may be used in the chewing gum compositions, include those flavors known to the skilled artisan, such as natural and artificial flavors. These flavorings may be chosen from synthetic flavor oils and flavoring aromatics and/or oils, oleoresins and extracts derived from plants, leaves, flowers, fruits, and so forth, and combinations thereof. Nonlimiting representative flavor oils include spearmint oil, cinnamon oil, oil of wintergreen (methyl salicylate), peppermint oil, Japanese mint oil, clove oil, bay oil, anise oil, eucalyptus oil, thyme oil, cedar leaf oil, oil of nutmeg, allspice, oil of sage, mace, oil of bitter almonds, and cassia oil. Also useful flavorings are artificial, natural and synthetic fruit flavors such as vanilla, and citrus oils including lemon, orange, lime, grapefruit, yazu, sudachi, and fruit essences including apple, pear, peach, grape, blueberry, strawberry, raspberry, cherry, plum, pineapple, watermelon, apricot, banana, melon, apricot, ume, cherry, raspberry, blackberry, tropical fruit, mango, mangosteen, pomegranate, papaya and so forth. Other potential flavors include a milk flavor, a butter flavor, a cheese flavor, a cream flavor, and a yogurt flavor; a vanilla flavor; tea or coffee flavors, such as a green tea flavor, a oolong tea flavor, a tea flavor, a cocoa flavor, a chocolate flavor, and a coffee flavor; mint flavors, such as a peppermint flavor, a spearmint flavor, and a Japanese mint flavor; spicy flavors, such as an asafetida flavor, an ajowan flavor, an anise flavor, an angelica flavor, a fennel flavor, an allspice flavor, a cinnamon flavor, a camomile flavor, a mustard flavor, a cardamom flavor, a caraway flavor, a cumin flavor, a clove flavor, a pepper flavor, a coriander flavor, a sassafras flavor, a savory flavor, a Zanthoxyli Fructus flavor, a perilla flavor, a juniper berry flavor, a ginger flavor, a star anise flavor, a horseradish flavor, a thyme flavor, a tarragon flavor, a dill flavor, a capsicum flavor, a nutmeg flavor, a basil flavor, a marjoram flavor, a rosemary flavor, a bayleaf flavor, and a wasabi (Japanese horseradish) flavor; alcoholic flavors, such as a wine flavor, a whisky flavor, a brandy flavor, a rum flavor, a gin flavor, and a liqueur flavor; floral flavors; and vegetable flavors, such as an onion flavor, a garlic flavor, a cabbage flavor, a carrot flavor, a celery flavor, mushroom flavor, and a tomato flavor. These flavoring agents may be used in liquid or solid form and may be used individually or in admixture. Commonly used flavors include mints such as peppermint, menthol, spearmint, artificial vanilla, cinnamon derivatives, and various fruit flavors, whether employed individually or in admixture. Flavors may also provide breath freshening properties, particularly the mint flavors when used in combination with cooling agents.

Other useful flavorings include aldehydes and esters such as cinnamyl acetate, cinnamaldehyde, citral diethylacetal, dihydrocarvyl acetate, eugenyl formate, p-methylamisol, and so forth may be used. Generally any flavoring or food additive such as those described in Chemicals Used in Food Processing, publication 1274, pages 63-258, by the National Academy of Sciences, may be used. This publication is incorporated herein by reference.

Further examples of aldehyde flavorings include but are not limited to acetaldehyde (apple), benzaldehyde (cherry, almond), anisic aldehyde (licorice, anise), cinnamic aldehyde (cinnamon), citral, i.e., alpha-citral (lemon, lime), neral, i.e., beta-citral (lemon, lime), decanal (orange, lemon), ethyl vanillin (vanilla, cream), heliotrope, i.e., piperonal (vanilla, cream), vanillin (vanilla, cream), alpha-amyl cinnamaldehyde (spicy fruity flavors), butyraldehyde (butter, cheese), valeraldehyde (butter, cheese), citronellal (modifies, many types), decanal (citrus fruits), aldehyde C-8 (citrus fruits), aldehyde C-9 (citrus fruits), aldehyde C-12 (citrus fruits), 2-ethyl butyraldehyde (berry fruits), hexenal, i.e., trans-2 (berry fruits), tolyl aldehyde (cherry, almond), veratraldehyde (vanilla), 2,6-dimethyl-5-heptenal, i.e., melonal (melon), 2,6-dimethyloctanal (green fruit), and 2-dodecenal (citrus, mandarin), cherry, grape, strawberry shortcake, and mixtures thereof.

In some embodiments, the flavor agent may be employed in either liquid form and/or dried form. When employed in the latter form, suitable drying means such as spray drying the oil may be used. Alternatively, the flavor agent may be absorbed onto water soluble materials, such as cellulose, starch, sugar, maltodextrin, gum arabic and so forth or may be encapsulated. The actual techniques for preparing such dried forms are well-known.

In some embodiments, the flavor agents may be used in many distinct physical forms well-known in the art to provide an initial burst of flavor and/or a prolonged sensation of flavor. Without being limited thereto, such physical forms include free forms, such as spray dried, powdered, beaded forms, encapsulated forms, and mixtures thereof.

In chewing gum compositions, flavor agents generally may be present in amounts from about 0.02% to about 5%, and more specifically from about 0.1% to about 4%, and even more specifically, from about 0.8% to about 3%, by weight of the composition.

Coloring agents may be used in amounts effective to produce the desired color. The coloring agents may include pigments which may be incorporated in amounts up to about 6%, by weight of the composition. For example, titanium dioxide may be incorporated in amounts up to about 2%, and preferably less than about 1%, by weight of the composition. The colorants may also include natural food colors and dyes suitable for food, drug and cosmetic applications. These colorants are known as F.D.& C. dyes and lakes. The materials acceptable for the foregoing uses are preferably water-soluble. Illustrative nonlimiting examples include the indigoid dye known as F.D.& C. Blue No. 2, which is the disodium salt of 5,5-indigotindisulfonic acid. Similarly, the dye known as F.D.& C. Green No. 1 comprises a triphenylmethane dye and is the monosodium salt of 4-[4-(N-ethyl-p-sulfoniumbenzylamino)diphenylmethylene]-[1-(N-ethyl-N-p-sulfoniumbenzyl)-delta-2,5-cyclohexadieneimine]. A full recitation of all F.D.& C. colorants and their corresponding chemical structures may be found in the Kirk-Othmer Encyclopedia of Chemical Technology, 3rd Edition, in volume 5 at pages 857-884, which text is incorporated herein by reference.

Sensates such as food Acids, Bicarbonate, cooling agents, intense sweeteners, warming agents, saliva stimulating agents, scrubbing particles can be incorporated. Colors including FD&C colors, EU Colors, Natural Colors and custom Pantone-matched colors can be also incorporated.

In some embodiments, the chewing gum compositions may include physiological cooling agents. A variety of well known cooling agents may be employed. For example, among the useful cooling agents are included xylitol, erythritol, dextrose, sorbitol, menthane, menthone, ketals, menthone ketals, menthone glycerol ketals, substituted p-menthanes, acyclic carboxamides, mono menthyl glutarate, substituted cyclohexanamides, substituted cyclohexane carboxamides, substituted ureas and sulfonamides, substituted menthanols, hydroxymethyl and hydroxymethyl derivatives of p-menthane, 2-mercapto-cyclo-decanone, hydroxycarboxylic acids with 2-6 carbon atoms, cyclohexanamides, menthyl acetate, menthyl salicylate, N,2,3-trimethyl-2-isopropyl butanamide (WS-23), N-ethyl-p-menthane-3-carboxamide (WS-3), isopulegol, 3-(1-menthoxy)propane-1,2-diol, 3-(1-menthoxy)-2-methylpropane-1,2-diol, p-menthane-2,3-diol, p-menthane-3,8-diol, 6-isopropyl-9-methyl-1,4-dioxaspiro[4,5]decane-2-methanol, menthyl succinate and its alkaline earth metal salts, trimethylcyclohexanol, N-ethyl-2-isopropyl-5-methylcyclohexanecarboxamide, Japanese mint oil, peppermint oil, 3-(1-menthoxy)ethan-1-ol, 3-(1-menthoxy)propan-1-ol, 3-(1-menthoxy)butan-1-ol, 1-menthylacetic acid N-ethylamide, 1-menthyl-4-hydroxypentanoate, 1-menthyl-3-hydroxybutyrate, N,2,3-trimethyl-2-(1-methylethyl)-butanamide, n-ethyl-t-2-c-6 nonadienamide, N,N-dimethyl menthyl succinamide, substituted p-menthanes, substituted p-menthane-carboxamides, 2-isopropanyl-5-methylcyclohexanol (from Hisamitsu Pharmaceuticals, hereinafter "isopregol"); menthone glycerol ketals (FEMA 3807, tradename FRESCOLAT® type MGA); 3-1-menthoxypropane-1,2-diol (from Takasago, FEMA 3784); and menthyl lactate; (from Haarman & Reimer, FEMA 3748, tradename FRESCOLAT® type ML), WS-30, WS-14, *Eucalyptus* extract (p-Mehtha-3,8-Diol), Menthol (its natural or synthetic derivatives), Menthol PG carbonate, Menthol EG carbonate, Menthol glyceryl ether, N-tertbutyl-p-menthane-3-carboxamide, P-menthane-3-carboxylic acid glycerol ester, Methyl-2-isopryl-bicyclo (2.2.1), Heptane-2-carboxamide; and Menthol methyl ether, and menthyl pyrrolidone carboxylate among others. These and other suitable cooling agents are further described in the following U.S. patents, all of which are incorporated in their entirety by reference hereto: U.S. Pat. Nos. 4,230,688; 4,032,661; 4,459,425; 4,136,163; 5,266,592; 6,627,233.

Some embodiments may include warming agents, which may be selected from a wide variety of compounds known to provide the sensory signal of warming to the individual user. These compounds offer the perceived sensation of warmth, particularly in the oral cavity, and often enhance the perception of flavors, sweeteners and other organoleptic components. Useful warming agents include those having at least one allyl vinyl component, which may bind to oral receptors. Examples of suitable warming agents include, but are not limited to: vanillyl alcohol n-butylether (TK-1000, supplied by Takasago Perfumery Company Ltd., Tokyo, Japan); vanillyl alcohol n-propylether; vanillyl alcohol isopropylether; vanillyl alcohol isobutylether; vanillyl alcohol n-aminoether; vanillyl alcohol isoamylether; vanillyl alcohol n-hexylether; vanillyl alcohol methylether; vanillyl alcohol ethylether; gingerol; shogaol; paradol; zingerone; capsaicin; dihydrocapsaicin; nordihydrocapsaicin; homocapsaicin; homodihydrocapsaicin; ethanol; isopropyl alcohol; iso-amylalcohol; benzyl alcohol; glycerine; chloroform; eugenol; cinnamon oil; cinnamic aldehyde; phosphate derivatives thereof; and combinations thereof.

Tingling agents may be employed to provide a tingling, stinging or numbing sensation to the user. Tingling agents include, but are not limited to: Jambu Oleoresin or para cress (*Spilanthes* sp.), in which the active ingredient is Spilanthol; Japanese pepper extract (*Zanthoxylum peperitum*), including the ingredients known as Saanshool-I, Saanshool-II and Sanshoamide; black pepper extract (*piper nigrum*), including the active ingredients chavicine and piperine; *Echinacea* extract; Northern Prickly Ash extract; and red pepper oleoresin. In some embodiments, alkylamides extracted from materials such as jambu or sanshool may be included. Additionally, in some embodiments, a sensation is created due to effervescence. Such effervescence is created by combining an alkaline material with an acidic material, either or both of which may be encapsulated. In some embodiments, an alkaline material may include alkali metal carbonates, alkali metal bicarbonates, alkaline earth metal carbonates, alkaline earth metal bicarbonates and mixtures thereof. In some embodiments, an acidic material may include acetic acid, adipic acid, ascorbic acid, butyric acid, citric acid, formic acid, fumaric acid, glyconic acid, lactic acid, phosphoric acid, malic acid, oxalic acid, succinic acid, tartaric acid and combinations thereof. Examples of "tingling" type sensates can be found in U.S. Pat. No. 6,780,443, the entire contents of which are incorporated herein by reference for all purposes. Tingling agents are described in U.S. Pat. No. 6,780,443 to Nakatsu et al., U.S. Pat. No. 5,407,665 to McLaughlin et al., U.S. Pat. No. 6,159,509 to Johnson et al. and U.S. Pat. No. 5,545,424 to Nakatsu et al., each of which is incorporated by reference herein in its entirety.

Oral care agents that may be used include those actives known to the skilled artisan, such as, but not limited to, surfactants, breath freshening agents, anti-microbial agents, antibacterial agents, anti-calculus agents, anti-plaque agents, oral malodor control agents, fluoride compounds, quaternary ammonium compounds, remineralization agents and combinations thereof.

The plasticizers, softening agents, mineral adjuvants, waxes and antioxidants discussed above, as being suitable for use in the gum base, may also be used in the chewing gum composition. Examples of other conventional additives which may be used include emulsifiers, such as lecithin and glyceryl monostearate, thickeners, used alone or in combination with other softeners, such as methyl cellulose, alginates, carrageenan, xanthan gum, gelatin, carob, tragacanth, locust bean, and carboxy methyl cellulose, acidulants such as malic acid, adipic acid, citric acid, tartaric acid, fumaric acid, and mixtures thereof, and fillers, such as those discussed above under the category of mineral adjuvants.

Other conventional gum additives known to one having ordinary skill in the chewing gum art also may be used in the chewing gum compositions.

Some embodiments extend to methods of preparing a chewing gum product. The products may be prepared using standard techniques and equipment known to those skilled in the art, which processes generally involve melting the gum base, incorporating the desired ingredients while mixing and forming the batch into individual chewing gum pieces. The apparatus useful in accordance with the embodiments described herein includes mixing and heating apparatus well known in the chewing gum manufacturing arts, and therefore the selection of the specific apparatus will be apparent to the artisan. For general chewing gum preparation processes see U.S. Pat. No. 4,271,197 to Hopkins et al, U.S. Pat. No. 4,352,822 to Cherukuri et al and U.S. Pat. No. 4,497,832 to Cherukuri et al, each of which is incorporated herein by reference in its entirety.

Individual chewing gum pieces may be formed using standard techniques known in the chewing gum art. For instance, chewing gum pieces may be prepared in the form of a slab, pellet, stick, center-fill gum, deposited, compressed chewing gum or any other suitable format.

For instance, center-fill chewing gum embodiments may include a center-fill region, which may be a liquid or powder or other solid, and a gum region. Some embodiments also may include an outer gum coating or shell, which typically provides a crunchiness to the piece when initially chewed. The outer coating or shell may at least partially surround the gum region.

Some other chewing gum embodiments may be in a compressed gum format, such as, for example, a pressed tablet gum. Such embodiments may include a particulate chewing gum base, which may include a compressible gum base composition and a tableting powder. Compressed chewing gums are more fully described in assignee's co-pending U.S. Provisional Application No. 60/734,680, filed on Nov. 8, 2005, and entitled "Compressible Gum System," the contents of which are incorporated herein by reference.

In some embodiments, the chewing gum may have a coating thereon. Such coated chewing gums are typically referred to as pellet gums. The outer coating may be hard or crunchy. Any suitable coating materials known to those skilled in the art may be employed. Typically, the outer coating may include sorbitol, maltitol, xylitol, isomalt, erythritol and other crystallizable polyols; sucrose may also be used. Furthermore the coating may include several opaque layers, such that the chewing gum composition is not visible through the coating itself, which can optionally be covered with a further one or more transparent layers for aesthetic, textural and protective purposes. The outer coating may also contain small amounts of water and gum arabic. The coating can be further coated with wax. The coating may be applied in a conventional manner by successive applications of a coating solution, with drying in between each coat. As the coating dries it usually becomes opaque and is usually white, though other colorants may be added. A polyol coating can be further coated with wax. The coating can further include colored flakes or speckles. If the composition includes a coating, it is possible that one or more oral care actives can be dispersed throughout the coating. This is especially preferred if one or more oral care actives is incompatible in a single phase composition with another of the actives. Flavors may also be added to yield unique product characteristics.

Other materials may be added to the coating to achieve desired properties. These materials may include without limitations, cellulosics such as carboxymethyl cellulose, gelatin, xanthan gum and gum arabic.

The coating composition may be applied by any method known in the art including the method described above. The coating composition may be present in an amount from about 2% to about 60%, more specifically from about 25% to about 45% by weight of the total chewing gum piece.

The oral delivery products of the present invention include an oral delivery composition forming the base of the product. The oral delivery composition may include, as explained above, chewing gum, non-chewing gum candy, edible films, and combinations thereof. Chewing gum compositions are preferred, but other non-chewing gum products may be useful in the invention. Further, combinations of chewing gums and non-chewing gum products, for example, a non-chewing gum candy having a chewing gum center (or vice versa), may be useful.

The oral delivery composition includes an orally deliverable base composition (also referred to herein as a "core" or "base" composition), which has at least one outer surface, which may include a coating or may be free of a coating. In preferred embodiments, the outer surface of the core is compositionally the same as the core product, and does not include a separate coating. In some embodiments, the outer surface may be the outer region of a center-filled product.

The product may include more than one outer surface, for example, a typical slab chewing gum product includes six outer surfaces. Any number of outer surfaces may be available in the present invention, as desired. Any of the outer surfaces may include one or more three dimensional objects, as will be described in more detail below, with some non-limiting examples seen in the Figures.

The oral delivery product of the present invention includes at least one three dimensional and edible object secured on the surface of the core composition. As defined herein, the term "secured" means that the object should remain in place and should not be easily removed during product manufacturing, packaging, transportation and shelf life. As will be described below, the three dimensional object may be removed through one or more other means, including, for example, product use (e.g., consumption by a user), water washing and direct application of heat, but it is desired that the object be secured such that it should reach the consumer without damage, deformation or removal from the product, and cannot easily be removed by routine force. This maintains the object on the surface of the product through packaging, shipping, handling, and storage, until consumption by the user.

The three dimensional object includes at least one binder material, such as a polymeric component, and a second component mixed therein, where the second component includes at least one deliverable component. The term "deliverable component" refers to a component that is delivered to the user through the product, and may include components such as flavors, colors, sweeteners, actives, sensates, effervescent compounds, and combinations thereof. The amount of deliverable component in the object may vary as desired. In instances where the amount of deliverable component is minimal, the product may include a greater amount of the three dimensional object so as to provide a desired amount of deliverable component to the user. It is particularly desired that the deliverable component be dispersed throughout the object in a substantially uniform manner.

The object may include more than one deliverable component. For example, the object may include a sensate and a flavor dispersed throughout the object. If desired, there may be a higher level of one deliverable component in the object than another deliverable component. The deliverable component may be in the form of a solid, liquid, powder, foam, suspension, gas, emulsion, and combinations thereof. The deliverable component may be free (i.e., non-encapsulated) or it may be encapsulated. Further, there may be a mixture of free and encapsulated deliverable component within the object. The resulting encapsulated material may be a capsule, bead, powder, or similar material. Desirably, the resulting encapsulated material has a particle size of less than about 3 mm in diameter. The object may include, in addition to a deliverable component, a binder material, fillers (including inorganic fillers), plasticizers, emulsifiers, surfactants, and combinations thereof.

In addition to the flavors, sensates, actives, and fillers explained above, the object may include any desired deliverable component. Suitable flavors include, but are not limited to, peppermint, spearmint, winter green, fruit, menthol, cinnamon, confectionary flavors and combinations thereof. Suitable sensates include those described above, and may include sensates such as those providing the sensation of effervescence, cooling, warming, tingling, scrubbing, bitterness, sourness, sweetness, foam, vapor action and combinations thereof. Various sensates may be used to provide a "sensorial experience" to a user, which means that the user experiences a particular sensation upon delivery of the component. Suitable actives include, for example, antibacterial, antimicrobial, breath freshening, herbal extract, tongue scrubbing micro particles, remineralization, mucoadhesive polymers, anti calculus, tooth whitening, anti plaque, vitamins, minerals, stimulants, food supplements, and combinations thereof.

The object includes a binder material, which may be hydrophilic, or it may include a combination of hydrophilic and hydrophobic properties. In preferred embodiments, the binder material is a meltable material, and most desirably is a polymeric material. For example, the object may include only hydrophilic polymers, or it may include both hydrophilic and hydrophobic polymers. The object desirably includes at least one polymeric material having a molecular weight of between 50 and 2,000,000 u, more desirably between about 1,000 and 30,000 u, and most desirably between about 2,000 and 10,000 u. In preferred embodiments, the polymer has a molecular weight of about 3,300 u. Any polymer may be used, including those described above. Preferably, the polymer used is polyethylene glycol, having a molecular weight of about 3,300 u. Other suitable polymers include, but are not limited to, hydroxypropylmethyl cellulose, hydroxyethyl cellulose, hydroxypropyl cellulose, methylcellulose, polyvinylpyrrolidone, carboxymethyl cellulose, polyvinyl alcohol, sodium alginate, xanthan gum, carrageenan gum, tragacanth gum, acacia gum, amylose, high amylose starch, hydroxypropylated, polydextose, high amylose starch, dextrin, pectin, chitin, chitosan, levan, elsinan, collagen, cyclodextrins, proteins, carbohydrates, polyols, vegetable gums, oligofructose, zein, gluten, soy protein isolate, whey protein isolate, casein, Guar gum, Gum Arabic, sodhydrogenated caster oil, shellac, cellulose derivatives, wax, PVA, pullulan, ethyl cellulose, gelatin, and combinations thereof.

The oral delivery composition forming the core of the delivery product may include at least one deliverable component, which may be the same or may be different from that in the object secured thereto. In some embodiments, the deliverable component in the object is the same as a deliverable component in the core, and thus the product provides an initial, rapid release of the deliverable component upon placing in the mouth, followed by a continuing residual release as the product is consumed by the user. For example, the deliverable component may be a flavor, and the same flavor may be contained in the object as well as the core. Upon placement in the mouth, the object begins to disintegrate in the presence of saliva, releasing the flavor and providing an initial, rapid sensation to the user. As the product is consumed, for example, by chewing the product, the flavor is released from the core, thereby providing a continued and prolonged release of the flavor to the user. In some preferred embodiments, the core is a chewing gum and the deliverable component is contained within the chewing gum. The deliverable component may be contained within the chewing gum in its encapsulated or its free form, or alternatively in both encapsulated and free forms.

In preferred embodiments, the three dimensional edible object may be deposited onto the surface of the chewing gum in the form of a flowable mixture, where the flowable mixture includes the binder material (for example, a meltable polymer) and any deliverable component(s) desired. After deposition, the object is solidified as described below.

It is desired that the flowable mixture include a polymeric material and have a viscosity of from about 1 cP to about 500,000 cP at deposition temperature. The resulting polymeric mixture should thus have characteristics and properties that allow the mixture to be deposited onto the surface of the chewing gum without the need for added solvents, and further to avoid undesired spreading prior to solidification. In some embodiments, the flowable mixture includes additional components, including fillers, but in other embodiments, the flowable mixture includes only the polymer(s) and deliverable component(s) mixed together.

Surfactants may be used in the polymeric mixture as solublizing, wetting or dispersing agents, which may aid in the disintegration of the object. Surfactants may be used to allow the object to release hydrophobic flavors/actives immediately. Some useful surfactants include sodium lecithin, tweens, lauryl sulfate, triacetin, CSL Calcium Stearoyl Di Laciate, PolyGlycerol Ester (PGE), Sorbitan Ester (SOE), PG Ester (PGME), Sugar Ester (SE), Monoglyceride (MG), Acetylated Monoglyceride (AMG), Lactylated Monoglyceride (LMG), GMS, and the like. One particularly useful surfactant is polaxamer 407 that is used as a solubilizing, wetting and dispersing agent.

Various fillers may optionally be used in the flowable mixture. Suitable fillers include, for example, sorbitol, maltitol, isomalt, mannitol, xylitol, erythritiol, sugar, polyols, alumina, talc, titanium dioxide, calcium stearate, magnesium stearate, zinc oxide, silica sand, clay, mica, various inorganic oxide pigments, magnesium oxide, dicalcium phosphate, calcium carbonate, silica, fumed silica mica, titanium dioxide.

The flowable mixture and resulting object are desirably free of added solvents, but may include a moisture level of up to 5% by weight, up to about 3% by weight, or more desirably up to 2% by weight. In some embodiments, the flowable mixture and resulting object include the polymer(s) and the deliverable component(s). In some embodiments, the flowable mixture and resulting object do not include any other component that may adversely affect the physical characteristics of the flowable mixture and resulting object, respectively. For example, the flowable mixture may only include a binder material, a deliverable component, and a sweetener. It is particularly desirable that all of the ingredients in the flowable mixture and resulting object are edible, and thus no non-edible ingredients should be used.

The polymer, and resulting object, may be generally hydrophilic in nature, and may have a solubility of greater than 0.1 g/ml. More particularly, the solubility of the object may be greater than 0.5 g/ml and may be up to 1.0 g/ml.

The object is desirably "readily disintegrable", which means that it is capable of initial disintegration at a rapid rate upon contact with a liquid, such as saliva. As used herein, a "rapid rate" means that its initial disintegration begins within less than 10 seconds, more desirably less than 5 seconds, and most desirably less than 2 seconds. Thus, the object "rapidly" begins to disintegrate in the presence of liquid, and releases components contained therein. A rapid disintegration is desired so that the deliverable component is released from the product rapidly. When the deliverable component is a sensate, the user feels an initial sensation provided by the sensate within this rapid delivery time. When the deliverable component is a flavor, the user feels an initial taste of flavor provided within this rapid delivery time. This is described as an initial "burst" of the component, e.g., a burst of flavor, a burst of sensate, a burst of sweetness, a burst of effervescence or sensory experience. It is, of course, understood that the terms "readily disintegrable", "rapid" rate of disintegration and "burst" are intended to describe the initial disintegration of the object, and not its complete disintegration. Complete disintegration may be much longer, and for example may be completed within about 30 to about 90 seconds, or may be even longer (i.e., up to about five minutes). Complete disintegration, as used herein, means at least 99% of the object is disintegrated. As used herein, the term "disintegration" is intended to include dissolution.

In some embodiments, the deliverable component may be delivered to the user upon placement within the mouth of the user. The deliverable component begins to be delivered to the user upon disintegration of the object, which may take place without chewing or with chewing or biting. For example, the disintegration of the object, and thus delivery of the deliverable component, may be achieved through sucking on the product without chewing. In some embodiments, the disintegration of the object may begin merely upon exposure to saliva and no action by the user is required beyond placement within the mouth.

The object is desirably a three dimensional object, such that it can be viewed and touched by the user. The object may rise above the surface upon which it is secured by a distance of about 0.01 mm to about 10 mm, and more specifically from about 0.1 mm to about 1 mm. The object may include regions where the depth is different. For example, at one portion of the product the depth of the object may rise from about 0.01 mm to about 0.05 mm, and at another portion of the product the depth of the object may rise from about 0.05 mm to about 1 mm.

The object may be any color desired, and may be transparent, may be translucent, or may be opaque. The object may be any pattern or image on the surface as desired. The object or objects may cover any desired amount of the surface of the composition and may take any desired shape or design. For example, the object may substantially cover the entire surface. For example, the object may be a series of dots, stripes, checkerboard patterns, stars, or any other recognizable shapes and patterns. The object may be a series of stripes that cover from about 5% to about 90% of the surface or a series of stripes that cover from about 5% to about 100% of the surface. The object may be a random arrangement of lines and other markings. Further, the object may be a recognizable object, such as a depiction of a real-life object or a word or series of words. The object may be a phrase, name, or other series of characters. The object may be a logo or other design that is associated with a person, product or company.

The surface may include more than one object secured thereto, and the objects may be different or they may be the same and they may include different components. Further, the objects on the same surface may include the same deliverable component or they may include different deliverable components. In some embodiments, one surface of a product may include a first object having a first deliverable component, and a second surface of a product may include a second object, having a second deliverable component, where the first and second deliverable components may be the same or may be different. Each surface of the product may include an object or more than one object, and the object(s) on each surface may be the same or may be different from that on another surface.

The three dimensional object (or objects) is secured to at least one surface in a sufficient amount that it may not be easily removed by force. The term "secured" as used herein, means that the object is sufficiently attached to the surface of the product such that the object(s) will not be unintentionally removed from the surface during manufacturing, packaging and prior to ultimate consumption by the user. Desirably, the object(s) are secured such that the object(s) should not be capable of being removed by a force under about 5 N. One method of testing the securement of the object(s) is by using a rudimentary peel test, such as a 90 degree peel test. In this method, household tape, such as Scotch® tape, is applied to the object, and then the tape is pulled at 90 degrees relative to the surface. If the object is removed with the tape, then the object is deemed to be insufficiently secured to the chewing gum surface. Desirably, the object is secured to a point that it passes the peel test, that is, that not more than about 5% to about 25% of the object is removed after application of Scotch® tape on the object and subsequent removal of the tape. That is, after the peel test, at least 75% to about 95% of the object remains secured to the surface.

Similarly, the object is desirably fracture resistant, such that the object and the pattern provided on the surface of the chewing gum product are not fractured or otherwise broken during manufacturing, packaging, handling and ultimate consumption by the user. Desirably, the object is not fractured upon placement of the product into a glass container, which is then subjected to vibrational forces.

In one embodiment of the invention, the object or objects on the surface of the product may be removed from the product without harming the core product. Methods of removal of the object are particularly useful when the core of the product is a chewing gum. Two methods of removing the object are provided, which may be used alternatively or cooperatively. The first method includes solvent (i.e., water) washing and the second is application of heat. In a water washing method, water is run over the surface of the chewing gum product such that the water is in contact with the object. Due to the ease of disintegration of the object, the object is disintegrated within a solvent, such as water or other polar solvent. Water may be run on the surface of the chewing gum product for a period of about 30 seconds to about 2 minutes, which may be modified to provide the desired removal level. Complete removal of the object is desired, but it is understood that minor amounts of residual object may remain on the surface (for example, less than 5% by weight of the original amount of the object may remain on the surface). The chewing gum composition is not substantially affected by the running water, and thus the chewing gum composition is not adversely affected. The remaining gum base may be re-used, for example, by placing the chewing gum composition into a mixing kettle where it may be melted and re-processed into a chewing gum composition.

The second removal method is through controlled and direct application of heat to the object. The melting point of the object is desirably lower than that of the oral delivery composition (e.g., a chewing gum), as will be explained in more detail below, and thus the application of heat to the object is useful in removing the object. Desirably, the chewing gum composition with object secured thereon is subjected to a level of heat that creates a temperature that falls between the melting point of the object and the melting point of the chewing gum. For example, if the melting point of the object is about 60° C. and the melting point of the chewing gum is about 100° C. or higher, the removal temperature may be between these temperatures.

Subjecting the product to such a temperature will melt the object and allow for its removal, while maintaining the chewing gum substantially intact. Complete removal of the object is desired, but it is understood that minor amounts of residual object may remain on the surface (for example, less than 5% by weight of the original amount of the object may remain on the surface). The underlying oral delivery composition (e.g., chewing gum) is not substantially affected by the heat applied, and thus the chewing gum product is not adversely affected. The remaining gum base may be re-used, for example, by placing the chewing gum into a mixing kettle where it may be melted and re-processed into a chewing gum.

A method of forming a product having at least one three dimensional object on a surface is also provided. Desirably, the product is a chewing gum product, but it is understood that other non-chewing gum products may be used as the base for the product.

An oral delivery composition, for example, a chewing gum or non-chewing gum composition, is first provided. The oral delivery composition may be formed through any desired means, including those described above. The oral delivery composition may include any components that are known to those of ordinary skill in the art. The oral delivery composition has at least one outer surface, which may or may not include a separate coating thereon. A typical slab gum, for example, includes six outer surfaces. Any number of surfaces may be used depending upon the shape of the oral delivery composition desired. The oral delivery composition forms the base or core of the inventive product.

Separately, a flowable mixture is formed. The flowable mixture includes at least one edible binder material, such as a polymer, and at least one deliverable component, as described above. Desirably, the flowable mixture is free of added solvent, but it may include moisture in levels of up to 5% by weight, more desirably less than 3% by weight of the mixture. Other components may be used, as described above, but it is particularly desirable that all components of the flowable mixture be edible.

The flowable mixture may include more than one deliverable component. For example, the flowable mixture may include a sensate and a flavor dispersed throughout the flowable mixture. If desired, there may be a higher level of one deliverable component in the flowable mixture than another deliverable component. The deliverable component may be free (i.e., non-encapsulated) or it may be encapsulated. Further, there may be a mixture of free and encapsulated deliverable component within the flowable mixture. The deliverable component may be in the form of a solid, liquid, powder, emulsion, and combinations thereof. The flowable mixture may be any color desired, and may be transparent, may be translucent, or may be opaque. The resulting object formed from the flowable mixture may likewise be transparent, translucent or opaque.

The flowable mixture may be hydrophilic, or it may include a combination of hydrophilic and hydrophobic properties. For example, the flowable mixture may include only hydrophilic polymers, or it may include both hydrophilic and hydrophobic polymers. Inclusion of a polymeric component forms a flowable polymeric mixture. The flowable polymeric mixture desirably includes at least one polymer having a molecular weight of between 50 and 2,000,000 u, more desirably between 1,000 and 30,000 u, more desirably between about 2,000 and 10,000 u, and most desirably between about 2,000 and 4,000 u. In preferred embodiments, the polymer has a molecular weight of about 3,300 u. Any polymer may be used, including those described above. Preferably, the polymer used is polyethylene glycol, having a molecular weight of about 3,300 u.

It is desired that the flowable polymeric mixture have a viscosity of from about 1 cP to about 500,000 cP at deposition temperature. The flowable polymeric mixture desirably has a solidification temperature of between about 20° to about 120° C., and more desirably about 40° C. to about 70° C., and most desirably between about 40° C. and 50° C. At a temperature above the solidification temperature, the flowable mixture remains flowable, and can thus be deposited onto the surface of the core composition. The solidification temperature of the flowable mixture may be lower or higher than the melting point of the oral delivery composition upon which the object is to be placed. In some embodiments, it may be preferred that the solidification temperature of the flowable mixture be lower than the solidification temperature of the oral delivery composition upon which the object is to be placed.

After the oral delivery composition (e.g., chewing gum composition) is formed into the desired shape, thus forming the core or base of the inventive product, the user selects the surface upon which the object is to be placed. The flowable mixture is heated to a temperature above the solidification temperature of the flowable mixture, but desirably a temperature below the melting point of the chewing gum composition. This allows the flowable mixture to be deposited onto the surface of the chewing gum composition without melting the chewing gum composition in the process. Preferably, the flowable mixture is heated to a temperature that is about 10° C. to about 20° C. above the solidification temperature of the flowable mixture. For example, if the solidification temperature of the flowable mixture is between 40° C. and 50° C., the deposition temperature may be between 60° C. and 70° C.

One the flowable mixture is heated to the desired temperature, the flowable mixture is deposited onto the surface of the composition and formed into in any pattern, image, or arrangement desired. For example, as explained above, the pattern may be a series of dots, stripes, checkerboard patterns, continuous or discontinuous lines, a random arrangement of lines and markings, a recognizable object, such as a depiction of a real-life object or a word or series of words, a phrase, name, or other series of characters, or a logo or other design that is associated with a person, product or company. More than one pattern may be deposited onto a given surface. The pattern may be laid down onto the surface in one action per side, but multiple actions may be acceptable. The pattern may be deposited to give any desired thickness for the resulting object, and more particularly may have a thickness of from 0.01 mm to about 10 mm as measured from the surface of the oral delivery composition to the top of the pattern.

Any method for depositing the flowable mixture may be used as desired, and may include non-contact methods or contact methods. Suitable non-contact methods include, for example, printing methods such as inkjet printing, screen printing or laminating. Other suitable methods include extruding, spraying, depositing, enrobing, embossing, casting, gravure, dipping, rolling, painting and three-dimensional printing, digital, thermal, laser, dye sublimation, dot matrix, stereo lithography, or flexographic methods.

The flowable mixture desirably has a sufficient viscosity during the deposition stage such that it does not spread out to an undesirable level after deposition and prior to solidification. It is preferred that the flowable mixture not spread more than about 20% of the area of deposition, and more preferably less than about 10% of the area of deposition. Preferred viscosity levels for the flowable mixture during the deposition stage are from about 10 to about 400,000 cP.

Once the flowable mixture is deposited onto the surface of the oral delivery composition as desired, the flowable mixture is allowed to cool. The oral delivery composition with flowable mixture deposited thereon is moved to an area having a temperature at or below the solidification temperature of the flowable mixture. In some embodiments, the area has a temperature about room temperature, and in some embodiments, the temperature is below room temperature. The use of fans, a cooling tunnel or other methods to lower the temperature of the flowable mixture may be used if desired. The flowable mixture is allowed to cool to a temperature at or below its solidification temperature as explained above. Once the flowable mixture cools, it forms a rigid three dimensional object secured to the oral delivery composition, as also explained above.

In one embodiment, the process of the invention uses a flowable mixture that is substantially free of added solvent. In this embodiment, the process avoids the need to evaporate solvents from the flowable mixture to form the rigid object. As is appreciated by those of skill in the art, solvent removal requires additional steps, such as application of heat, vacuum, or an extended period of time. All that is required in the present invention is cooling the flowable mixture to its solidification temperature. Further, the level of deposition of the flowable mixture is variable, and allows for a thicker deposition or thinner deposition, and thus the level of deliverable component may be controlled and varied from product to product without altering the formulation for the flowable mixture.

Other objects may be deposited on at least one other surface of the oral delivery composition by following the steps outlined above. Each surface may include an object secured thereto, or one or more surfaces may include objects. Further, a first object may be disposed and secured to the surface of a second object, for example one object on top of another. Further, a different object may be deposited onto different surfaces, where the different objects include a different pattern or a different deliverable component. For example, one surface may include an object including an effervescing component, and a second surface of the same product may include an object including a flavor. Other combinations are understood by those of skill in the art.

In one particular embodiment, the inventive process may include the step of removing the rigid and secured object without harming or compromising the core composition to which the object is secured. As used herein, the step of removing the object from the surface of the core composition does not necessarily mean complete and total removal, but rather it is understood that a minor amount of the object may remain after the removal step. For example, less than 5% of the object may remain, or less than 3% of the object may remain, or less than 2% of the object may remain. In addition, during and after the step of removing the object from the surface, the core composition is not harmed. Subsequent to the step of removing the object, the core composition may be re-used to form another core composition. This is particularly useful when the core composition is a chewing gum composition.

The present invention contemplates two methods of removing the object from a chewing gum composition. The first is water washing and the second is application of heat. In a water washing method, water, or other edible solvent, is run over the surface of the chewing gum composition such that the water or other edible solvent is in contact with the object. Due to the ease of disintegration of the object, the object is disintegrated within the water. Water may be run on the surface of the chewing gum composition for a period of about 10 seconds to about 5 minutes, more specifically from about 30 seconds to about 2 minutes, which may be modified to provide the desired removal level. Complete removal of the object is desired, but it is understood that minor amounts of residual object may remain on the surface as previously explained. Since water is used in this process, and the chewing gum composition is a generally hydrophobic material, the chewing gum composition is not substantially affected by the running water. The remaining gum base may be re-used, for example, by placing the chewing gum composition into a mixing kettle where it may be melted and re-processed into a chewing gum composition. In some embodiments, the chewing gum composition need not be reprocessed into another composition, and the steps of depositing a rigid object on the surface of the same chewing gum composition may be repeated.

The second removal method is through application of heat to the object. The melting point of the rigid object is less than that of the core composition, as will be explained in more detail below, and thus the application of heat to the object is useful in removing the object. In this method, the core composition with object secured thereon is subjected to a level of heat that falls between the melting point of the object and the melting point of the core composition. For example, the core composition may be a chewing gum having a melting point that is higher than the melting point of the object, and the heat applied creates a temperature that falls between these two melting point levels.

Subjecting a chewing gum composition to such a temperature will melt the object and allow for its removal, while maintaining the chewing gum substantially intact. Complete removal of the object is desired, but it is understood that minor amounts of residual object may remain on the surface as previously explained. The chewing gum composition is not substantially affected by the heat applied, and thus the chewing gum composition is not adversely affected. The remaining gum base may be re-used, for example, by placing the chewing gum composition into a mixing kettle where it may be melted and re-processed into a chewing gum composition. In some embodiments, the chewing gum composition need not be reprocessed into another composition, and the steps of depositing a rigid object on the surface of the same chewing gum composition may be repeated.

In some embodiments, the step of removing the object may take place after the flowable mixture has hardened and become secured to the core surface as a rigid object, or it may take place prior to the step of cooling the flowable mixture. For example, during processing, the edible core composition having at least one surface is first formed. Separately, a flowable mixture is formed as described above. The flowable mixture is deposited onto the surface of the core composition, as also described above. If it is determined that the pattern or patterns deposited onto the surface of the composition are not acceptable, the flowable mixture may be removed prior to cooling the flowable polymeric mixture. Alternatively, the flowable polymeric mixture may be cooled to form a rigid object secured to the surface of the oral delivery composition. Subsequently, if it is determined that the pattern or patterns deposited onto the surface of the composition are not acceptable or desirable, the rigid object may be removed as explained above. The resulting composition with object removed may be re-used or re-processed as explained above.

In some embodiments, the product may include an object on more than one surface of the oral delivery composition. To form such a product, the steps of depositing and cooling a flowable mixture on a first surface are performed. Once the first rigid object on the first surface is formed, i.e., through cooling the deposited mixture, the steps of depositing and cooling a flowable mixture on a second surface of the same core composition may be performed. The steps may be repeated to deposit objects on as many surfaces of the composition as may be desired. Further, the step of removing the object explained above may be performed on one or more than one of the surfaces containing an object.

The present invention further provides a method of providing a release, or rapid release (i.e., a "burst", as explained above) of a deliverable component or a sensorial experience to a user. In this embodiment, an oral delivery core composition having at least one object on at least one surface is provided as explained above. The core composition may be, for example, a chewing gum composition, a non-chewing gum composition, or an edible film composition. Of course, more than one object may be provided on one surface or multiple surfaces, and more than one deliverable component may be provided in one object or in more than one object. In some embodiments, the object may completely cover one surface or all of the surfaces of the core composition, thus enrobing the core composition.

The core composition having at least one object having at least one deliverable component is placed into the mouth of a user, and the object (or objects) is allowed to disintegrate in the presence of saliva. The deliverable component is thereby released from the object and into the mouth of the user. The deliverable component is desirably "rapidly" released from the object, which means that the object begins to disintegrate and release the deliverable component within less than 10-20 seconds, and more desirably less than 5 seconds after exposure to liquid, such as saliva. In some embodiments, at least 50% of the deliverable component is released from the object within about 90 seconds after exposure to liquid, or more desirably within about 60 seconds after exposure to liquid either with or without chewing or biting the product. In other embodiments, at least 75% of the deliverable component is released from the object within about 2 minutes after exposure to liquid, or within about 90 seconds after exposure to liquid, or within about 60 seconds after exposure to liquid either with or without chewing or biting the product. The deliverable component may include any component described above, including, for example, flavors, colors, sweeteners, sensates, effervescing compounds and combinations thereof.

The release of the deliverable component may be achieved merely by placing the inventive product into the mouth of the user and thus exposing the object(s) to saliva, or the user may perform an action to increase the rate of disintegration of the object. For example, the user may suck on the product, or the user may chew or bite on the product. In some embodiments, the user may suck on the product for a sufficient time to disintegrate the object and then subsequently chew the product.

In general, an orally disintegrable three dimensional pattern, containing a hydrophilic polymer and flavor and or active ingredient deposited onto a flat confectionery or gum surface is prepared. The three dimensional pattern is useful for quick or immediate release of deliverable components in the mouth. A quick release of certain components is reached through a special matrix from water-soluble polymers. Formulation considerations such as emulsifiers, plasticizers, fillers, are factors that may affect the mechanical properties of the films, such as shifting the glass transition temperature to lower temperature.

A desirable composition of the present invention contains one or more of the following characteristics: patterns, shapes and designs in various sizes and shapes, rapid disintegration and release, no added solvent in the object, enhanced stability of components, and improved release of active components, when used.

EXAMPLES

Preparation of a Three Dimensional Object
1. Quick Disintegrable PEG Composition Deposited on a Slab Gum Approximately 93.8 g of powdered PEG (polyethylene glycol) 3300 was melted in a beaker using a microwave heater. To this melted polymer, approximately 1 g of Aspartame, 1 g of Menthol, 5 g of Maltitol and 0.2 g of coloring were added and mixed well. The mixture was kept at approximately 60° C. using a water bath. About 0.5 g of the mixed PEG composition was then deposited on a slab gum surface using a deposable pipette and allowed to solidify at room temperature for 24 hrs. The resulting object was well adhered to the gum. Only one side was exposed.

2. Quick Disintegrable Polyethylene (PE) Wax—Alginate Composition Deposited on a Slab Gum Approximately 73 g of powdered Polyethylene wax was melted in a beaker using a microwave heater. About 20 g of sodium alginate powder containing 1% menthol, 1 g of Aspartame, 0.8 g of Menthol, 5 g of Maltitol and 0.2 g of coloring were added and mixed well. The mixture was kept at 80° C. using a water bath. About 0.5 g of the PE wax composition was deposited on the surface of a slab gum using a pipette, and then allowed to solidify at room temperature for 24 hrs. The resulting object was well adhered to the gum. Only one side was exposed.

3. Quick Disintegrable Fat—Gum Arabic Composition Deposited on a Slab Gum

Approximately 73 g of powdered hydrogenated fat was melted in a beaker using a microwave heater. About 20 g of Gum Arabic powder containing 1% menthol, 1 g of Aspartame, 0.8 g of Menthol, 5 g of Maltitol and 0.2 g of coloring were added and mixed well. The resulting mixture was kept at 80° C. using a water bath. Approximately 0.5 g of the hydrogenated fat composition was deposited on the surface of a slab gum using a pipette, and then allowed to solidify at room temperature for 24 hrs. The resulting object was well adhered to the gum. Only one side was exposed.

4. Disintegration and Flavor Tests

Various slab gum compositions including aspartame were prepared. A control slab chewing gum with no deposited three dimensional object, and including 1% aspartame, was prepared. Three test slab chewing gums were prepared, each including a three dimensional object adhered to one surface. The three dimensional object compositions were prepared according to the Table 1 below:

TABLE 1

| Ingredients | PEG Composition (%) | PE wax - Alginate Composition (%) | PEG-Gum Arabic Gum Composition (%) |
|---|---|---|---|
| PEG 3300 | 92.3 | 0 | 0 |
| Poly ethylene Wax | 0 | 72.5 | 0 |
| Sodium Alginate | 0 | 20 | 0 |
| Gum Arabic | 0 | 0 | 20 |
| Aspartame | 1 | 1 | 1 |
| Menthol | 1 | 0.8 | 0.8 |
| Maltitol | 5 | 5 | 5 |
| Blue color | 0.2 | 0.2 | 0.2 |
| Lecithin | 0.5 | 0.5 | 0.5 |
| Hydrogenated Fat | 0 | 0 | 72.5 |
| Total | 100 | 100 | 100 |

The slab gum was prepared as set forth in the Table 2 below:

TABLE 2

| Components | Wt. % |
|---|---|
| Gum base | 35 |
| Lecithin | 0.5 |

TABLE 2-continued

| Components | Wt. % |
|---|---|
| Sorbitol | 56.5 |
| Aspartame | 1 |
| Glycerin | 5 |
| Flavor | 2 |
| Total | 100 |

The control slab gum was prepared with the components above and no object secured to its surface. The test gums were prepared according to Examples 1-3 above, with one including a PEG composition, one including a PE-Alginate composition, and one including a hydrogenated fat—gum arabic composition. The compositions of the three test gums are in the Table above.

The dissolution procedure was performed as follows: The gum was placed on the bottom of a 500 ml beaker equipped with an impeller. The gum surface containing the object was facing up to maximize contact with the dissolution medium. As quickly as possible, about 300 ml of phosphate buffer pH 7 and 37° C. (+/−0.5° C.) was poured in the beaker containing the gum. When the water completely covered the gum the impeller was started stifling at 250 rpm. After about 5 seconds a timer was started, then 5 ml of samples were taken at 10, 20 and 30 seconds respectively. Each sample was filtered to remove solids and poured into a cuvette. The amount of Aspartame in each sample was determined using UV/Vis spectrophotometer at 210 nm absorption wavelength.

Figure 1:
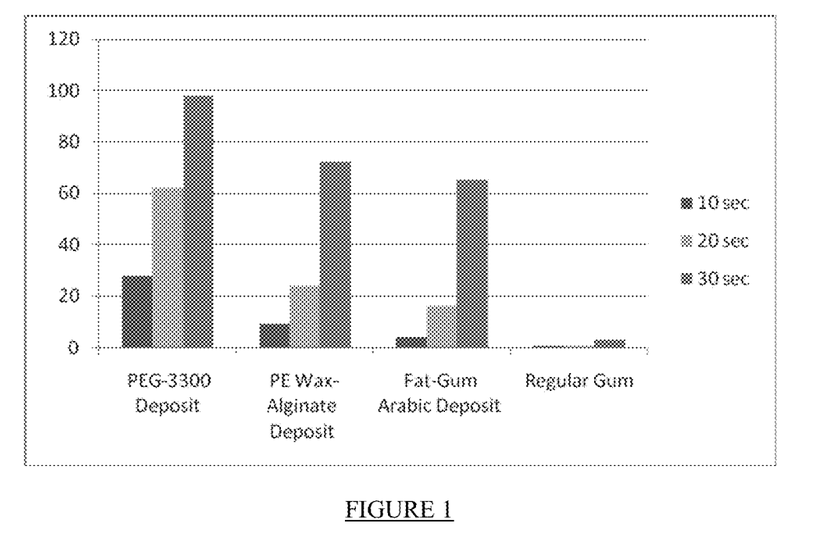
FIG. 1 shows the dissolution profiles of aspartame from various deposited compositions on slab chewing gums and a slab chewing gum without deposited compositions.

The dissolution profiles of the four gums (PEG, PE-Alginate, Fat-Gum Arabic, and Non-covered gum) are provided as FIG. 1. As can be seen, the dissolution profile of the three products including three-dimensional objects on one surface is significantly higher than that of the control gum. This is true at 10 seconds and 20 seconds, and most significantly, at 30 seconds. It was found that each object on the test gums was completely dissolved in the beaker using the impeller, as described above, within 80 seconds.

Figure 2:
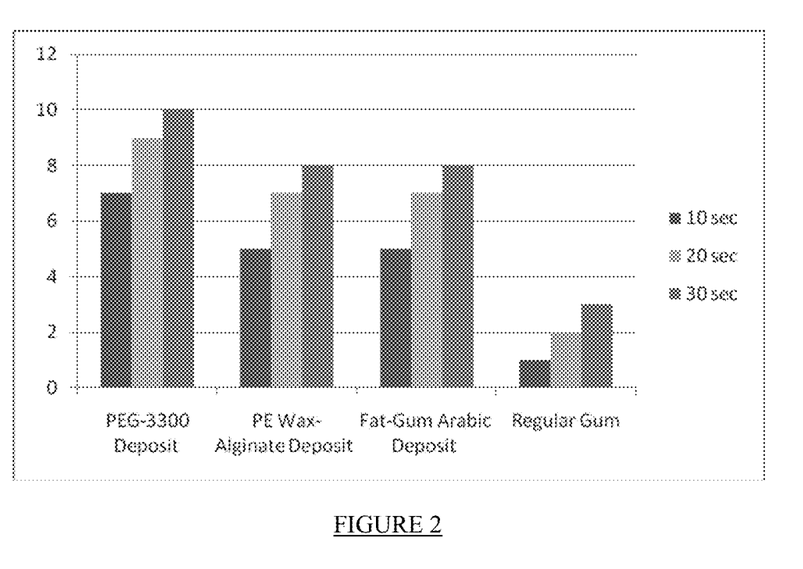
FIG. 2 shows the flavor intensity of various deposited compositions on a slab chewing gum.
Figure 3:
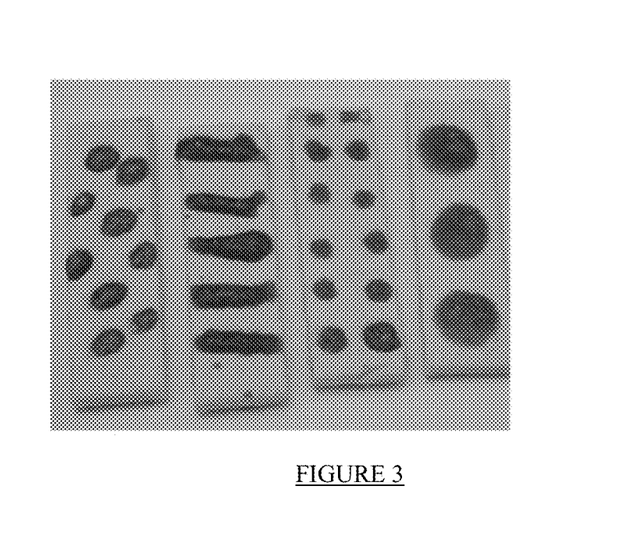
FIG. 3 shows several exemplary patterns for deposited objects on a confectionery product.
Figure 4:
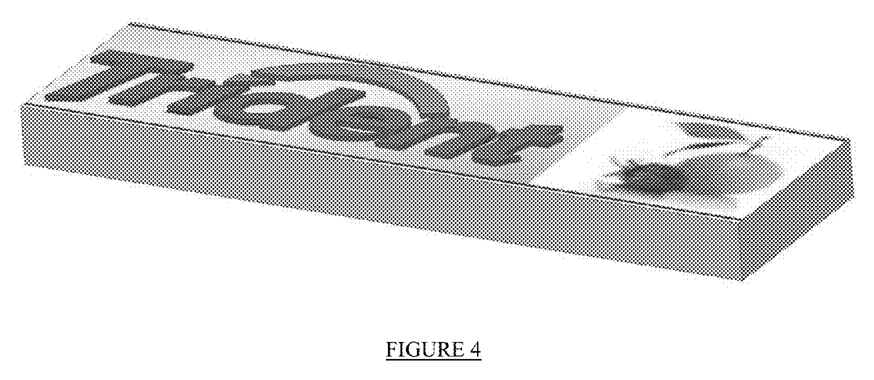
FIG. 4 shows one embodiment with a three dimensional object being a word and logo.
Figure 5:
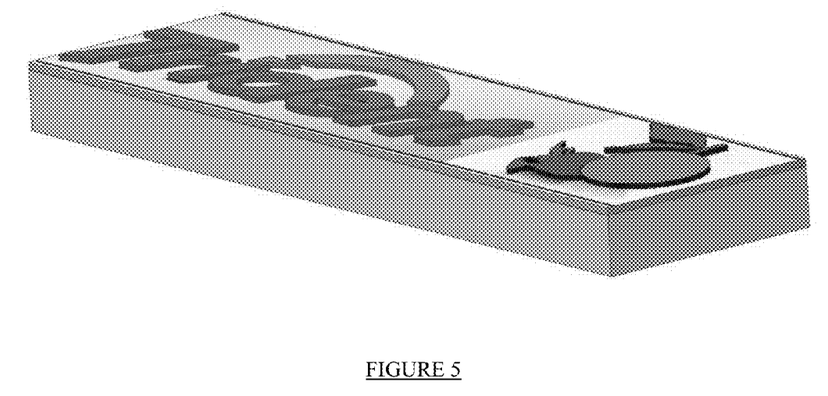
FIG. 5 shows another embodiment with a three dimensional object being a word and logo.

The gums including deposited compositions, as well as the control gum, were placed onto the top of the tongue of a user and allowed to disintegrate without mastication. Each gum was placed in the mouth of a subject and rolled around in the mouth without chewing or biting. The flavor intensity was evaluated on a scale of 1-12, with 12 being the most intense and 1 being least intense. Intensity measurements were taken at 10 seconds, 20 seconds and 30 seconds. The results are set forth in FIG. 2. The intensity profiles of the object-containing products are significantly higher than that of the control gum, and further it can be seen that the PEG-based object had the highest flavor intensity at all three time periods.

5. Three Dimensional Objects to Deliver a Component

Various three dimensional objects may be prepared including sensates, flavors, anti-bacterial agents, effervescing agents, spray dried flavors, flavor microcapsules, and other similar components. Examples of useful three dimensional object formulations include the following, with all percentages being weight percent:

Example A

Menthol

| | % |
|---|---|
| PEG 3300 | 87 |
| Menthol | 1 |
| Sweetener | 1 |
| Maltitol | 10 |
| Color | 1 |
| Total | 100 |

Example B

Peppermint Flavor

| | % |
|---|---|
| PEG 4000 | 93 |
| Pepper Mint Flavor | 3 |
| Aspartame | 0.7 |
| Ace K | 0.3 |
| Titanium Dioxide | 1 |
| Color | 2 |
| Total | 100 |

Example C

Fruit Flavor

| | % |
|---|---|
| PEG 10000 | 80 |
| Orange flavor | 5 |
| Sucralose | 1 |
| Citric acid | 3 |
| Color | 2 |
| Xylitol | 9 |
| Total | 100 |

Example D

Effervescent Composition

| | % |
|---|---|
| PEG 3300 | 84 |
| Menthol | 5 |
| Sweetener | 1 |
| Bicarbonate | 3 |
| Citric acid | 2 |
| Color | 2 |
| Clay | 3 |
| Total | 100 |

Example E

Spray Dried Flavor

|  | % |
|---|---|
| PEG 3300 | 88 |
| Spray dried mint Favor | 6 |
| Sweetener | 1 |
| Mica | 3 |
| Color | 2 |
| Total | 100 |

Example F

Flavor Microcapsules

|  | % |
|---|---|
| PEG 3300 | 87 |
| Microcapsules containing Flavor | 10 |
| Sweetener | 1 |
| Color | 2 |
| Total | 100 |

Example G

Anti Bacterial Composition

|  | % |
|---|---|
| PEG 8000 | 90 |
| Gantrez | 1 |
| Magnolia Bark extract | 1 |
| Lauric Arginate (LAE) | 1 |
| Zinc oxide | 3 |
| Sweetener | 1 |
| Titanium Oxide | 3 |
| Total | 100 |

Example H

Cooling Composition

|  | % |
|---|---|
| Wax | 50 |
| Erythritol | 24 |
| Xylitol | 20 |
| Glycerin | 1 |
| Flavor | 2 |
| Intense Sweetener | 1 |
| Titanium Oxide | 2 |
| Total | 100 |

Example I

Tongue Scrubbing Composition

|  | % |
|---|---|
| Fat | 50 |
| Silica | 24 |
| Clay | 20 |
| Glycerin | 1 |
| Flavor | 2 |
| Sweetener | 1 |
| Titanium Oxide | 2 |
| Total | 100 |

The above examples are simply to demonstrate various potential releasable and deliverable components, and are not intended to be limiting of the full scope of the invention. It is understood that other releasable and deliverable components may be used in the invention through the use of formulations such as those above.

What is claimed is:

1. A chewing gum product comprising:
a. a chewing gum composition having at least one outer surface; and
b. at least one edible, three dimensional object secured to said at least one outer surface, comprising;
 i. a meltable, polymeric binder material comprising a mixture of hydrophilic and hydrophobic polymers; and
 ii. a deliverable component, wherein the deliverable component is encapsulated;
 wherein the three dimensional object is a pattern or image on said at least one outer surface; and
 wherein the object is readily disintegrable upon contact with saliva, thereby releasing the deliverable component comprised therein.

2. The chewing gum product of claim 1, wherein said deliverable component is selected from the group consisting of flavors, colors, sweeteners, actives, sensates, inorganic fillers, plasticizers, emulsifiers, surfactants, and combinations thereof.

3. The chewing gum product of claim 2, wherein said active is selected from the group consisting of antibacterial agents, antimicrobial agents, breath freshening agents, herbal extract, tongue scrubbing micro particles, remineralization agents, anti calculus agents, tooth whitening agents, anti plaque agents, vitamins, minerals, stimulants, food supplements, and combinations thereof.

4. The chewing gum product of claim 1, wherein said deliverable component is one of a liquid, a solid, a foam, a suspension, or an emulsion.

5. The chewing gum product of claim 1, wherein said meltable, polymeric binder material has a molecular weight of about 50 to about 2,000,000 u.

6. The chewing gum product of claim 1, wherein said meltable, polymeric binder material comprises polyethylene glycol.

7. The chewing gum product of claim 6, wherein said polyethylene glycol has a molecular weight of from about 1,000 to about 30,000 u.

8. The chewing gum product of claim 1, wherein the deliverable component is encapsulated in an encapsulation system, and wherein the encapsulation system is selected from the group consisting of a capsule, a granule, a bead and a fine powder.

9. The chewing gum product of claim 8, wherein the deliverable component is selected from the group consisting of flavors, colors, sweeteners, actives, sensates, inorganic fillers, plasticizers, emulsifiers, surfactants, and combinations thereof.

10. The chewing gum product of claim 8, wherein the encapsulation system provides an encapsulated component having a particle size of less than about 3 mm in diameter.

11. The chewing gum product of claim 1, wherein the object begins to disintegrate in presence of saliva within less than 10 seconds.

12. The chewing gum product of claim 1, wherein said object includes a pattern selected from the group of a series of dots, a series of stripes covering from about 5% to about 90% of said surface, random lines, a logo or word, or a combination thereof.

13. The chewing gum product of claim 1, wherein said object is transparent, translucent, or opaque.

14. The chewing gum product of claim 1, wherein said object has a height as measured from said surface of 0.01 mm to 10 mm.

15. The chewing gum product of claim 14, wherein said object has a height as measured from said surface of 0.1 mm to 1.0 mm.

16. The chewing gum product of claim 1, wherein said object is free of added solvent.

17. The chewing gum product of claim 16, wherein the object includes less than 5% moisture.

18. The chewing gum product of claim 1, wherein said object is secured to the surface such that it passes a 90 degree peel test.

19. The chewing gum product of claim 1, comprising more than one object on said surface.

20. The chewing gum product of claim 19, wherein a first object having a first deliverable component and a second object having a second deliverable component are secured to said surface, and said first and second deliverable components are different from each other.

21. The chewing gum product of claim 1, wherein said object may be removed from surface without destroying said chewing gum composition.

22. The chewing gum product of claim 21, wherein said step of removing the object is performed by water washing said surface.

23. The chewing gum product of claim 21, wherein said step of removing the object is performed by heating said surface to a temperature that is above the melting point of said object but lower than the melting point of said chewing gum composition.

24. The chewing gum product of claim 1, wherein said object is flowable at a temperature of about 20° C. to about 120° C.

25. The chewing gum product of claim 1, wherein said object is flowable at a temperature of about 50° C. to about 60° C.

26. The chewing gum product of claim 1, wherein said object solidifies at a temperature of below 50° C.

27. The chewing gum product of claim 1, wherein said object solidifies at a temperature of about 40° C. to about 50° C.

* * * * *